(12) United States Patent
Bouvyn (10) Patent No.: US 6,650,959 B1
(45) Date of Patent: Nov. 18, 2003

(54) METHOD AND APPARATUS FOR THE DETECTION OF FOREIGN MATERIALS IN MOVING TEXTILE MATERIALS

(75) Inventor: Patrick Bouvyn, Waregem (BE)

(73) Assignee: Barco N.V. (BE)

( * ) Notice: Subject to any disclaimer, the term of this patent is extended or adjusted under 35 U.S.C. 154(b) by 0 days.

(21) Appl. No.: 09/521,778

(22) Filed: Mar. 9, 2000

Related U.S. Application Data
(60) Provisional application No. 60/123,717, filed on Mar. 10, 1999.

(30) Foreign Application Priority Data

Mar. 10, 1999 (EP) .............................................. 99870041

(51) Int. Cl.[7] .......................... G06F 19/00; G01N 33/36
(52) U.S. Cl. ........................ 700/143; 324/454; 324/456; 73/159; 73/160
(58) Field of Search ................................ 700/129, 139, 700/142, 143, 144, 130; 19/0.2, 80 R; 324/71.1, 109, 123 R, 452, 454, 456; 34/561; 340/675, 677; 73/159, 160; 209/127.1

(56) References Cited

U.S. PATENT DOCUMENTS

| | | | | |
|---|---|---|---|---|
| 1,922,933 A | * | 8/1933 | Dirks .......................... | 324/454 |
| 2,189,352 A | * | 2/1940 | Siegenheim ................ | 324/454 |
| 4,041,375 A | * | 8/1977 | Polukhina et al. .......... | 324/454 |
| 4,707,887 A | | 11/1987 | Leifeld et al. ................ | 19/0.2 |
| 5,287,061 A | * | 2/1994 | Dechene et al. ............ | 324/454 |
| 5,448,172 A | * | 9/1995 | Dechene et al. ............ | 324/454 |

FOREIGN PATENT DOCUMENTS

| | | |
|---|---|---|
| DE | 38 07 355 | 12/1988 |
| DE | 195 35 177 | 3/1997 |
| EP | 0 652 432 | 5/1995 |
| WO | WO 98/33061 | 7/1998 |

OTHER PUBLICATIONS

Derwent Publications Ltd., London, GB; AN 88082471, XP002111227; SU 1 328 748 Chem Fibres Process; Feb. 14, 1985.

* cited by examiner

*Primary Examiner*—Leo Picard
*Assistant Examiner*—Steven R. Garland
(74) *Attorney, Agent, or Firm*—Bacon & Thomas, PLLC (57) ABSTRACT

A method and an apparatus for detecting foreign fibers in a moving textile material, in particular in moving threads, yarns or slivers, include providing a probe for picking up triboelectric signals from the moving textile material and comparing the output of the probe with a reference value to provide a signal representative of detection of a foreign fiber in the textile material. The apparatus may be used in a card, a drawing bench, a ring spinning machine, an air-jet spinning machine, an open-end spinning machine, a chemical spinning machine, a bobbin winding machine a doubling machine, a combing machine, a bobbin frame, a texturing machine or a loom.

24 Claims, 11 Drawing Sheets

METHOD AND APPARATUS FOR THE DETECTION OF FOREIGN MATERIALS IN MOVING TEXTILE MATERIALS

This applications claims the benefit of provisional application 60/123,717 filed Mar. 10, 1999.

The present invention relates to a method and an apparatus for the detection of foreign materials in moving textile materials, in particular to the detection of foreign fibres or foreign materials in moving yarns, threads, slivers, and unformed fibre bands, cords, ropes, including monofilament and multifilament threads. The present invention may find advantageous use in all sorts of textile machinery, including, but not limited to, weaving or knitting or spinning machines, in particular, ring-, open-end-, air-jet- or chemical spinning machines, bobbin winding machines, carding machines, drawing benches, combing machines, bobbin frames or texturing machines.

TECHNICAL BACKGROUND

Various methods of detecting foreign fibres in moving textile materials have been described, for example, those based on optical methods. WO 98/33061 and EP-A-652 432 are examples of such methods. These methods are excellent but generally require the selection of frequencies of light which are able to distinguish foreign materials from the virgin thread material. Sometimes this is difficult if the colour and/or light absorbency of both the foreign and the virgin fibre are very similar.

Triboelectric detection heads have been used for determining the presence of the movement of threads or fibres as disclosed in U.S. Pat. No. 3,676,769 or U.S. Pat. No. 4,027,232. These include a probe which picks up electrical signals from the moving thread or yarn. The electrical signal generated by relative movement between a textile thread and an object is best described as a form of noise. This undifferentiated signal has found use in deciding if a yarn or thread is broken, i.e. if relative movement has stopped.

It is known that different materials provide different triboelectric voltages and/or currents. U.S. Pat. No. 5,341,103 describes a method of measuring the triboelectric charge on a moving flexible strip of material of short length. U.S. Pat. No. 4,885,543 describes a method of measuring triboelectric voltages on bulk materials. As explained in this latter document the results of triboelectric testing of different materials is often unreliable due to the great variations in values. A further aspect which is clearly demonstrated from the test results in this document is that many materials hold their triboelectric charge for a considerable length of time, e.g. 120 seconds or more. This is well known in processing industries where the charging up of moving sheets is a major cause of concern. It also means that any measurement of triboelectricity depends upon the previous history of the material being tested. This can be a source of unreliability and variability in the measurements.

It is an object of the present invention to provide a method and an apparatus for the detection of foreign materials in moving textile materials which allows detection even when the foreign material is optically almost identical to that of the virgin fibre.

In particular, it is an object of the present invention to provide a method and an apparatus for the detection of foreign materials in moving textile materials which can be used in existing textile machines without requiring a redesign of such equipment.

SUMMARY OF THE INVENTION

The present invention includes the use of a triboelectric probe to detect foreign materials in a moving textile material, in particular in moving threads, yarns or slivers.

The present invention may provide a method for detecting foreign materials in a moving textile material, in particular in moving threads, yarns or slivers, comprising the steps of:

generating relative motion between the textile material and a probe;

measuring electric signals picked up by the probe from the textile material;

comparing the measured electric signals with a value representative of the textile material without foreign material; and determining from the comparison whether foreign material is present in the textile material.

The present invention may include an apparatus for detecting foreign materials in a moving textile material, in particular in moving threads, yarns or slivers, comprising: a probe for picking up electric signals from the textile material; a comparator for comparing the output of the probe with a reference value and being adapted to provide a signal representative of detection of a foreign material in the textile material.

The dependent claims define further individual embodiments of the present invention.

The present invention, its advantages and embodiments will now be described with reference to the following drawings.

DESCRIPTION OF THE ILLUSTRATIVE EMBODIMENTS

The present invention will be described with reference to specific embodiments and certain drawings but the invention is not limited thereto but only by the claims.

A particularly difficult type of foreign matter which is preferably removed from slivers, threads or yarns is the inclusion of thin white polypropylene (PP) strips into cotton. These fibres originate from the packing bags used to transport the cotton and the strips are typically 10 mm to 50 mm long or longer and about 0.1 mm wide. They often are first noticed in the dyeing stage at which time they appear as white faults as they do not absorb the dyes used for cotton. The PP strips may be wound around the circumference of the yarn or may be laid-in longitudinally. Despite many attempts it has not been possible to entirely remove this form of contamination.

A first embodiments of a foreign material detector 40 in accordance with the present invention will be described with reference to FIG. 1. A triboelectric sensor 41 is provided which picks up electrical signals from a moving textile material 5 such as a thread, yarn or sliver by being galvanically, dielectrically or capacitively coupled to the textile material 5. Sensor 41 may include any known triboelectric probe, e.g. as described in U.S. Pat. No. 3,676,769 or U.S. Pat. No. 4,027,232 or may include any of the specific electrode arrangements in accordance with the present invention as discussed below. The sensor 41 outputs its signal 24 to a measuring circuit 43 which provides conventional adjustments to the signal such as any one of high pass, low pass or band pass analog or digital filtering, gain control and optionally rectification. Measuring circuit 43 is preferably adapted so that it particularly selects those frequencies, frequency bands, and/or amplitude ranges which preferentially discriminate for foreign materials over signals generated by the textile material 5. The selection of the upper and lower cut-off frequencies of the filters in measuring circuit 43 may be set by a frequency band selector 42. The output signal from the measuring circuit 43 is fed in parallel to an extraction circuit 44 and a comparator 45. In the extraction circuit 44, a value for the base noise signal for the textile material 5 is extracted over a suitable period of time. The time period should be chosen such that signals from occasional foreign fibres or material do not alter the base noise value appreciably. For instance, the extraction circuit 44 may determine the standard deviation of the measured triboelectric yarn noise signal over a suitable length of textile material, e.g. 50 meters. The amplitude of the base noise signal from the textile material may vary with time due to changes in humidity, changes in temperature, changes in quality of the textile material, changes in speed and/or tension of the textile material, changes in the speed of rotation of bobbins as the amount of textile material on the bobbin reduces, etc. Hence, it is preferred in accordance with the present invention if the base noise signal is continuously monitored, e.g. by a running average standard deviation. This base noise signal value is fed to the comparator 45 which also receives at least one pre-set difference value from a pre-set difference value circuit 46. In the comparator 45 the signal from the measuring circuit 43 is compared with the base noise level and the pre-set difference value. When the measured value exceeds the base noise level by an amount which exceeds the pre-set difference value, the comparator 45 outputs a foreign material signal to decision circuit 47. For example, the peak-to-peak value of the measured triboelectric signal may be normalised in the comparator circuit 45 with respect to the base noise signal before being compared with the pre-set value. For instance, the ratio of the peak-to-peak voltage to the standard deviation of the yarn noise signal may be calculated in the comparator 45 and compared to the pre-set value from circuit 46. When the ratio exceeds the pre-set value a foreign material signal is output from circuit 45 to the decision circuit 47.

The present invention also includes provision of two or more pre-set values to the comparator 45, for instance upper and lower set values which define a band in which normalised triboelectric signals from foreign matter in the textile material are known to fall. These pre-set values are preferably selectable by the user in accordance with the textile material and the known type of foreign material present therein.

The decision making circuit 47 may be a simple relay which switches off the machine when the comparator 45 outputs a foreign material detect signal. Preferably, the decision circuit 47 includes sufficient local intelligence (processor capacity) to make a more balanced judgement of the presence of foreign matter. There may be several extraneous reasons why the signal from the measuring circuit 43 may change. For instance, it may indicate a knot or change in diameter of the textile materials, a change in the quality of the textile material, a change in the humidity or temperature, a change in speed of the textile material, etc. The decision circuit 47 may receive inputs from other sensors 48, e.g. textile speed sensors, optical textile material diameter or thickness sensors, other foreign body sensors, etc. and may then make a final decision as to whether foreign material is probably present or not based on consideration of all these sensor inputs. The output of the decision circuit 47 confirming a foreign material may be used to carry out suitable alterations to the process, e.g. stop the textile material to allow inspection, or to automatically cut out the relevant section and join the cut ends. The decision circuit 47 may also optionally deactivate the triboelectric foreign material detection during automatic splicing of the yarn if unsteady results are obtained at this time.

Figure 2:
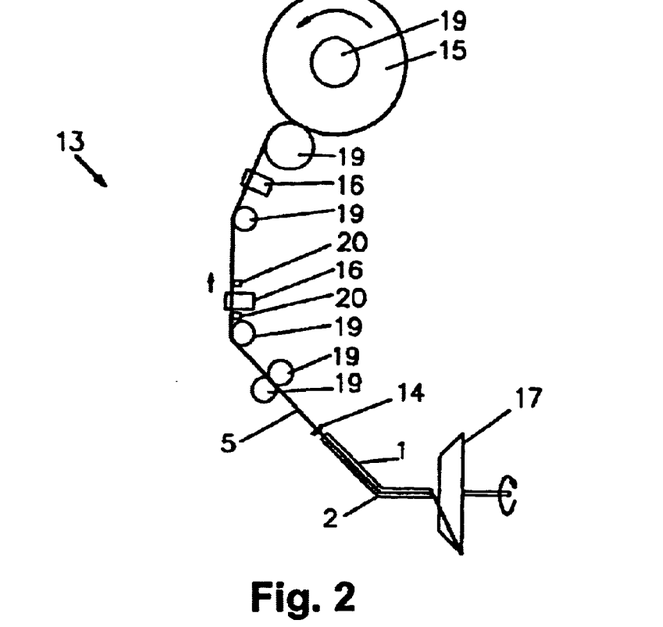
FIG. 2 is a schematic representation of the yarn path in an open-end spinning machine.

In the following further detailed examples of embodiments of the present invention will be described with reference to an open-end spinning machine, e.g. a Schlafhorst Autocoro 288 running cotton yarn of diameter 0.27 mm at a speed of 160 m/min. FIG. 2 shows a diagrammatic illustration of the path of the yarn 5 in an open-end spinning machine. In the following text, a discussion is given, as a typical application of the invention, of a detector for detecting foreign fibres and foreign materials in the textile material 5, which is a yarn spun on an open-end spinning machine. A person skilled in the art is able to modify this embodiment for other applications, such as other types of spinning machines, bobbin winding machines, doubling machines, cards, combing machines, texturing machines, weaving machines.

Known detectors 16 are usually placed on an open-end spinning machine in the path of the yarn between the navel 14 and the bobbin 15. The yarn 5 is wound onto the bobbin 15 from the navel 14 via drive and guide rolls 19. Owing to their position, known detectors 16 in the path of the yarn 5 are always provided with some form of slot, along which the yarn 5 is introduced into the measurement slot of the detector 16. Supports 20 ensure that the position of the yarn 5 in a detector 16 is stable. In accordance with the present invention, detectors of foreign fibres may be integrated with the equipment for measuring other properties of the yarn 5, e.g. diameter or mass. In particular the detector in accordance with the present invention may be integrated with a conventional triboelectric yarn-break device.

In addition to being placed in the path of the yarn 5, a detector 40 in accordance with the present invention can also be placed on open-end spinning machines between the navel 14 and the rotor 17 itself, for instance on or in the so-called "spinning tube" 1, a tubular element which is essential to the open-end spinning process and forms a channel which guides the yarn 5 outwards from the rotor 17. For instance, the detector may be placed on the spinning tube 1 or integrated therewith, for instance by being placed at the torque stop 2. This has a number of advantages.

- it can be used on open-end spinning machines of any design
- self-cleaning properties, owing to the subatmospheric pressure from the rotor 17 and owing to the friction of the yarn 5.
- material of the spinning tube 1 can be selected as a function of the requirements of the detector 40
- abundance of space
- inherent protection from ambient influences.

Spinning process demands, such as a specific finish, are placed on the inner wall of the spinning tube 1. The only demands which the spinning machine places on the outer circumference of the spinning tube 1 are technical assembly demands. For this reason, the components of the detector 1 may be arranged on the outer circumference of the spinning tube 18. This means that the material forming the spinning tube 1 must be suitable for extracting the electrical signals from the yarn 5. In accordance with embodiments of the present invention, the material of the spinning tube 1 may be at least partly of insulating or conductive materials. There is sufficient space and capacity to supplement and adapt the spinning tube 1 for the mounting of a foreign material detector 40.

Optionally, the present invention includes a plurality of detectors in the yarn path to provide additional security as to the determination of foreign matter in the yarn 5.

Figure 1:
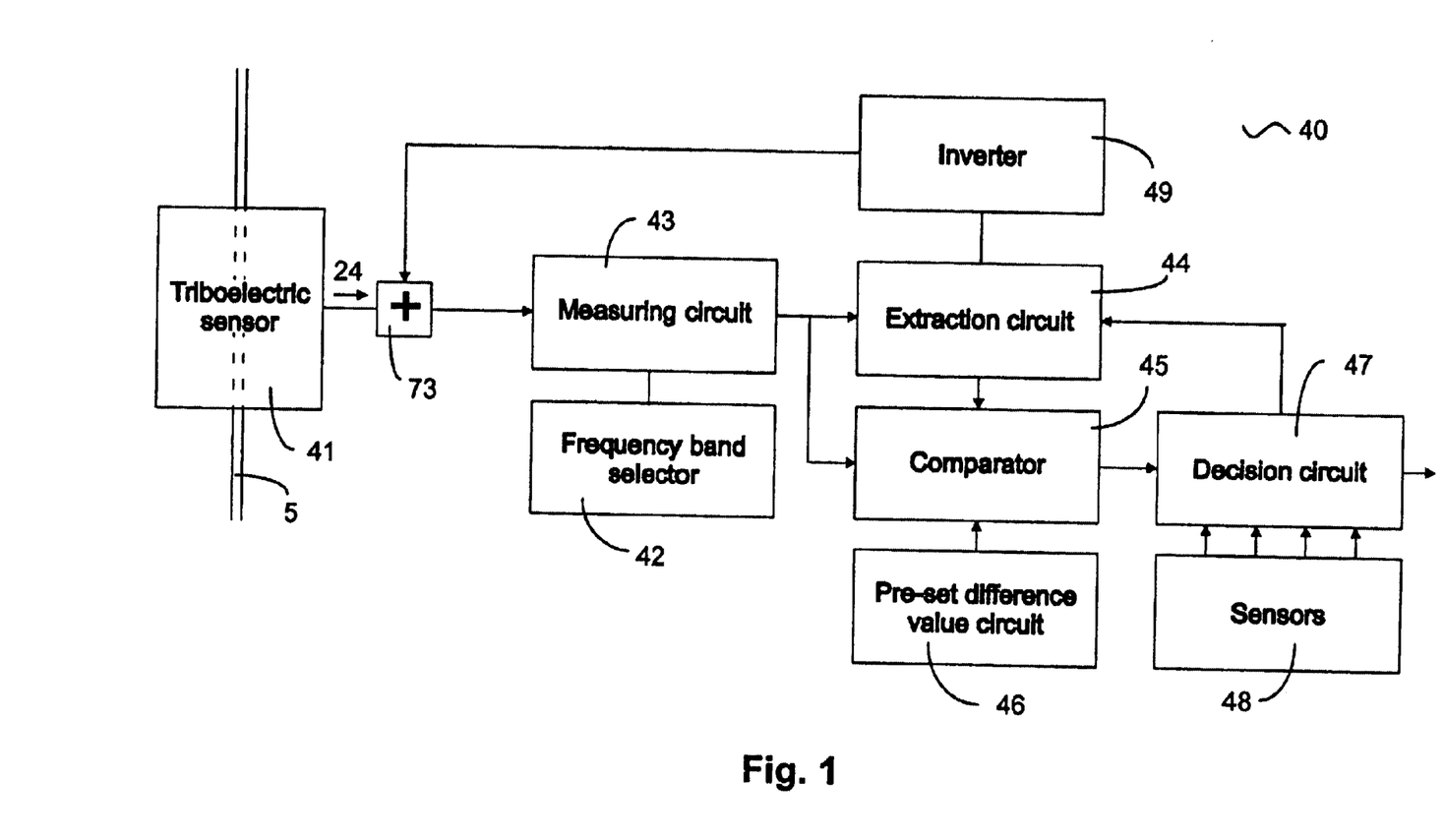
FIG. 1 is a schematic circuit diagram representation of a detector in accordance with an embodiment of the present invention.
Figure 3A:
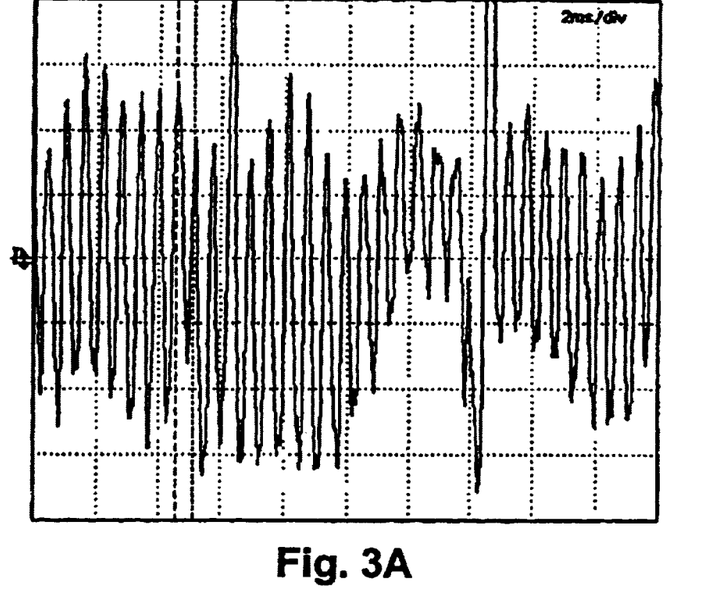
FIGS. 3A and B show traces triboelectric signals picked up from a cotton yarn from close to the rotor and remote from the rotor, respectively, in an open-end spinning machine showing periodic signals imposed on the yarn noise signal.
Figure 3B:
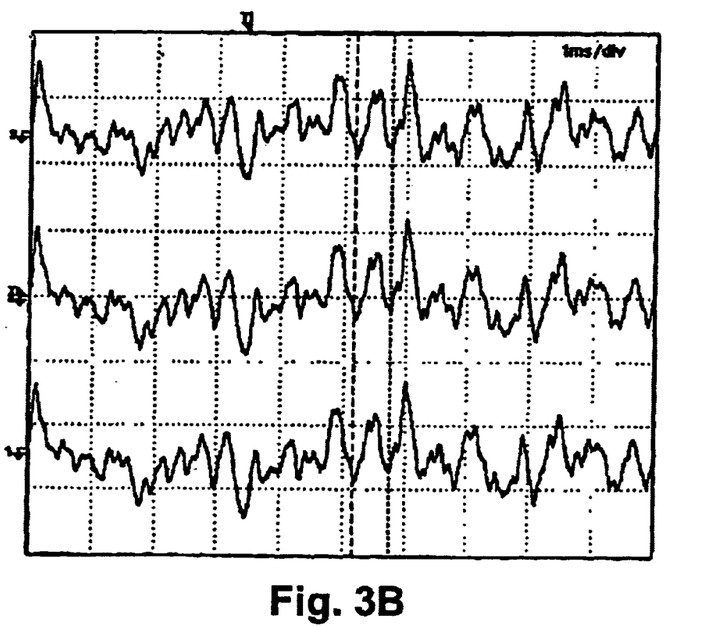

With reference to FIG. 1, the present invention also optionally includes the provision of a periodic signal cancelling circuit and a method step of cancelling periodic signals from the output of the triboelectric sensor 41. It has been determined from experiment that the output of the sensor 41 may include periodic signals generated for instance by rotational movement of components of a spinning machine. FIG. 3A shows the triboelectric signal output of an electrode in galvanic contact with the yarn 5 placed at the torque step 2 of the spinning tube 1 of the spinning machine of FIG. 2. The signal has a frequency component of 1.7 kHz which corresponds to the rotation frequency of the rotor 17. FIG. 3B shows that some periodicity is still present in signals from a detector placed in the outer yarn path from the navel 14 to the bobbin 15. In accordance with an embodiment of the present invention such periodic signals may be cancelled. For instance, the extraction circuit 44 may include circuitry to acquire and track periodic signals. Circuits for acquiring and tracking periodic signals are well known to the skilled person and may include a phase-locked-loop and a dither circuit. The component of the output signal of the measuring circuit 43 with the periodic signal may be extracted by the extraction circuit 44, inverted, phase delayed or advanced and gain adjusted in an inverter 49 and added (adder 73) to the output of the sensor 41 to cancel the periodic signal. The necessary input of the frequency of the periodic signal to the extraction circuit 44 may be provided by the decision circuit 47 based on pre-set or pre-measured values or based on the signals detected by the sensors 48, e.g. the output of a sensor sensing the frequency of rotation of rotor 17.

Various electrode arrangements for sensing electric signals from the yarn 5 are included as individual embodiments of the present invention and are described below. Also described below and included as individual embodiments of the present invention is the placement of the electrodes at specific positions of a spinning machine or similar. Also described below and included as separate embodiments of the present invention are various measurement circuits suitable for picking up the electric signals from the yarn 5.

Figure 4:
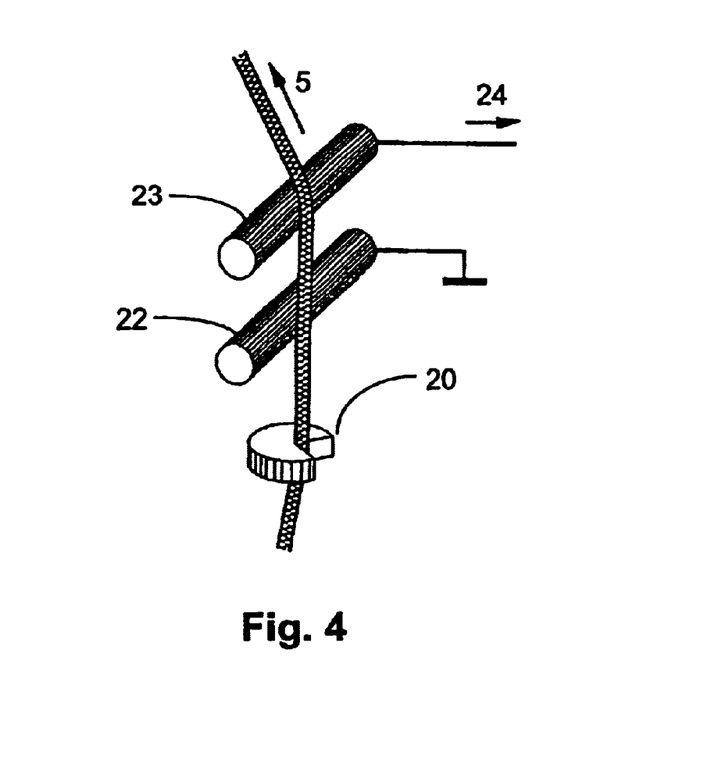
FIGS. 4 to 9 show schematic electrode arrangements in accordance with embodiments of the present invention.

A first type of electrode arrangement in accordance with the present invention is shown schematically in FIG. 4. It may be placed in the outer yarn path between the navel 14 and the bobbin 15. The arrangement comprises two cylindrical electrodes 22, 23 sequentially mounted with respect to the yarn movement direction. These electrodes 22, 23 may have a nominal diameter of 1.5 mm and may be separated by a distance of 9 mm. The first electrode 22 is made of conductive material such as steel and is earthed. It is in galvanic contact with the yarn 5 and serves to strip charge from the yarn 5 before detection by the pick-up electrode 23. The pick-up electrode 23 may be conductive, e.g. made of steel, and in galvanic contact with the yarn 5 or may be insulated from the yarn, e.g. by a glass layer or by a layer of air. In the latter case the pick-up electrode 23 is dielectrically coupled to the yarn 5. Lateral movements of the yarn may be reduced or prevented by a yarn guide 20 made of alumina ceramic or similar.

The galvanically coupled electrode 23 can pick-up signals 24 from the yarn 5 from DC to the frequency cut-off of the measurement circuit connected to the electrode 23. The dielectrically coupled electrode 23 has a low frequency cut-off of about 1 kHz.

Figure 5:
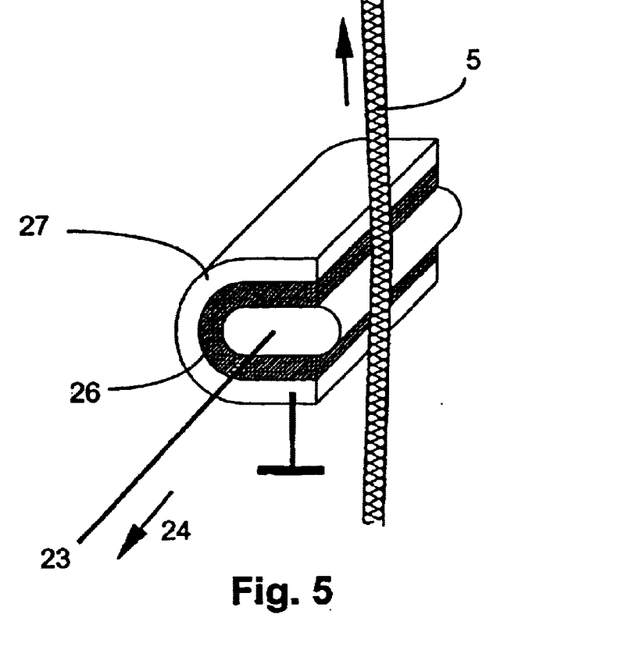

A second type of electrode arrangement in accordance with the present invention is shown schematically in FIG. 5. Electrical signals from yarn 5 are picked up on a conductive, e.g. nickel, electrode 23 which is in galvanic contact with the yarn 5. The pick-up electrode 23 is also the output electrode for the signal 24. The pick-up electrode 23 is shielded by an earthed conductive shield 27 which is insulated from the electrode 23 by an insulating layer 26.

Figure 6:
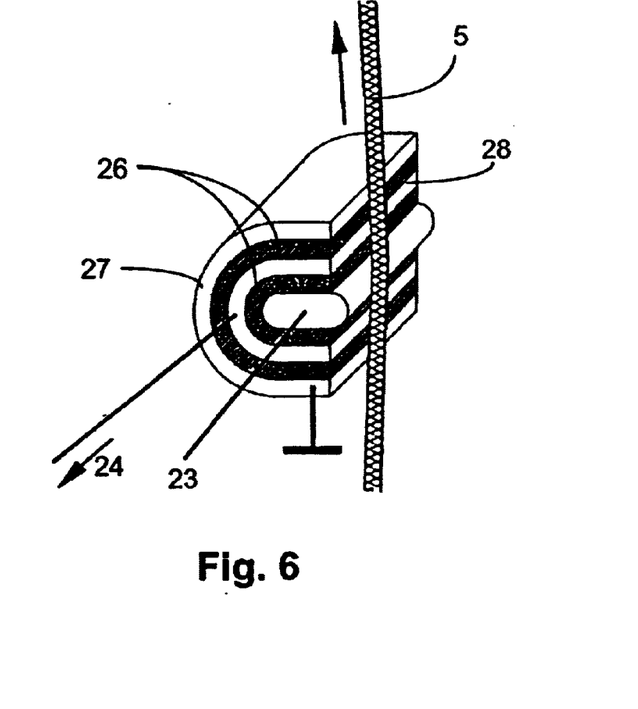

A third type of electrode arrangement in accordance with the present invention is shown schematically in FIG. 6. It includes a pick-up electrode 23 in contact with yarn 5 and which is insulated from an output electrode 28 by an insulating layer 26. The pick-up electrode 23 may be made from silicon carbide. The whole assembly is shielded by an earthed conductive shield 27. The signal 24 is taken from the output electrode 28 which is capacitively linked to the pick-up electrode 23.

Figure 7:
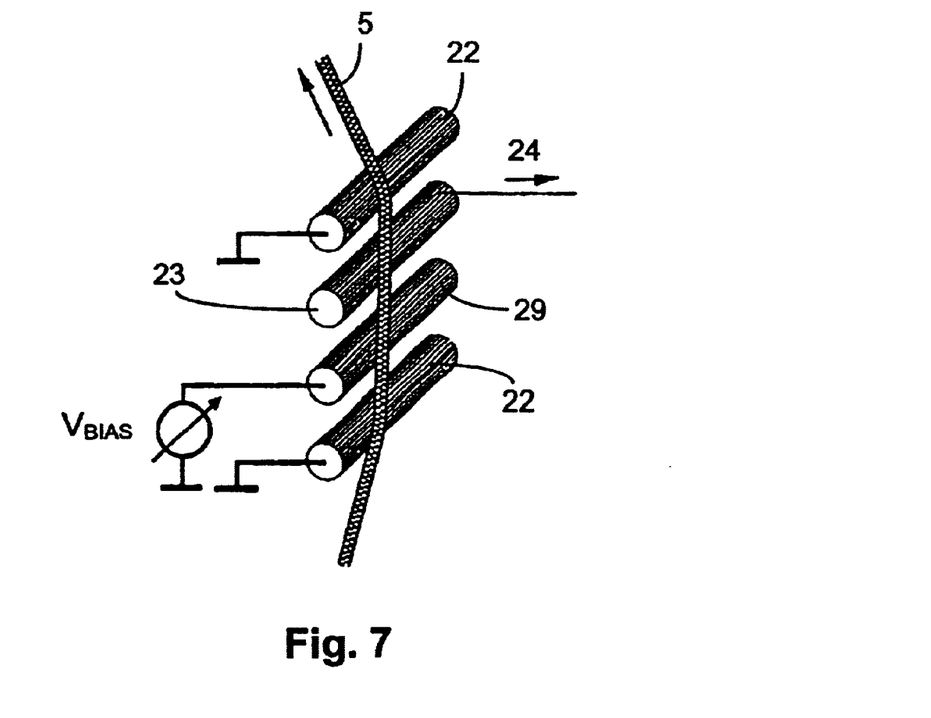

A fourth type of electrode arrangement in accordance with the present invention is shown schematically in FIG. 7. It includes a sequence of electrodes 22, 23, 29 placed along the yarn path and which may be made of steel. The pick-up electrode 23 is in galvanic contact with the yarn 5 and also serves as the output electrode for signal 24. The charge stripping electrodes 22 are maintained at earth potential and are used to remove triboelectric charge from the yarn 5, particularly before detection. An optional additional electrode 29 may be placed under a bias voltage which may be at earth potential or a positive or negative potential.

Figure 8:
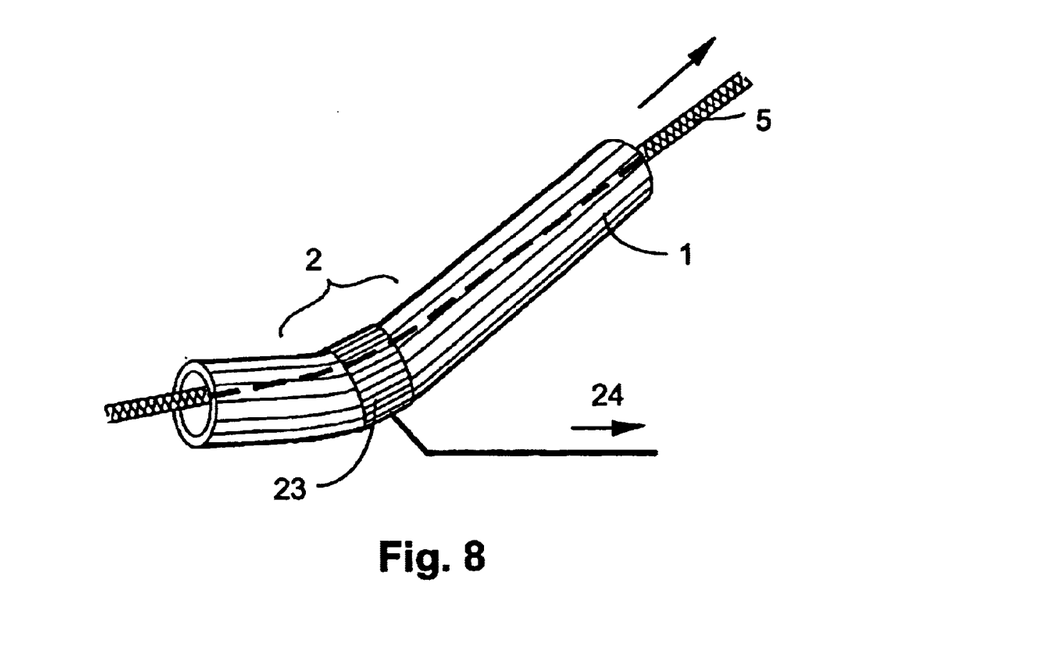

A fifth type of electrode arrangement is shown schematically in FIG. 8. It includes a pick-up electrode 23 placed at the torque stop 2 of a spinning tube 1. The electrode 23 may be made of copper and may be on the surface of the torque stop 2 in which case it is dielectrically coupled to yarn 5 passing through the spinning tube 1 or may be set into the torque stop 2 so that it is in galvanic contact with the yarn 5. To form a galvanic contact a 2 mm long brass cylinder was mounted between two parts of the spinning tube 1. For the dielectrically coupled electrode 23, a 2 mm wide copper foil was attached to the outside of the spinning tube 1. The spinning tube 1 was made of alumina ceramic and was about 1.5 mm thick.

Figure 9:
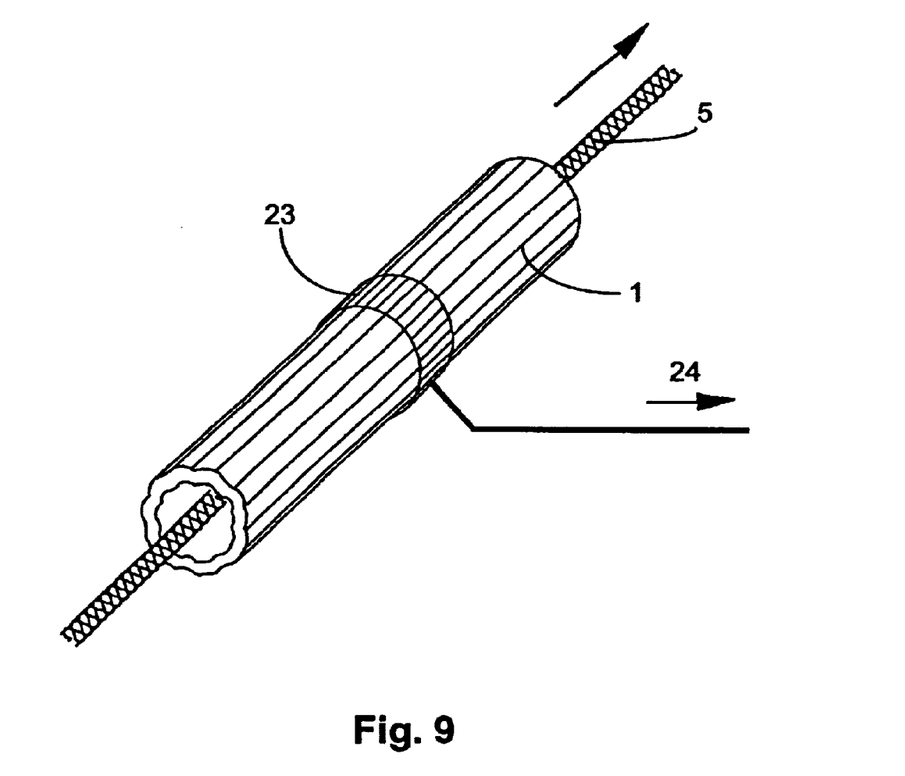

Yet a further electrode arrangement in accordance with the present invention is shown schematically in FIG. 9. It shows a conductive ring electrode 23 placed around an insulating guide such as the spinning tube 1. The electrode 23 is dielectrically coupled to the yarn 5 passing through the spinning tube 1. The electrode 23 may be formed of 2 mm wide copper foil placed on the outside of the spinning tube 1. The spinning tube may be made of an insulating material such as ABS plastic.

The present invention also includes one or more earthed charge stripping electrodes placed along the yarn path before the detection point. It has been found advantageous to reduce or eliminate charge historically built up on the yarn 5 before measurement. This can best be achieved by contact with several conductive earthed electrodes some of which may be remote from the detecting device in accordance with the present invention.

Figure 10:
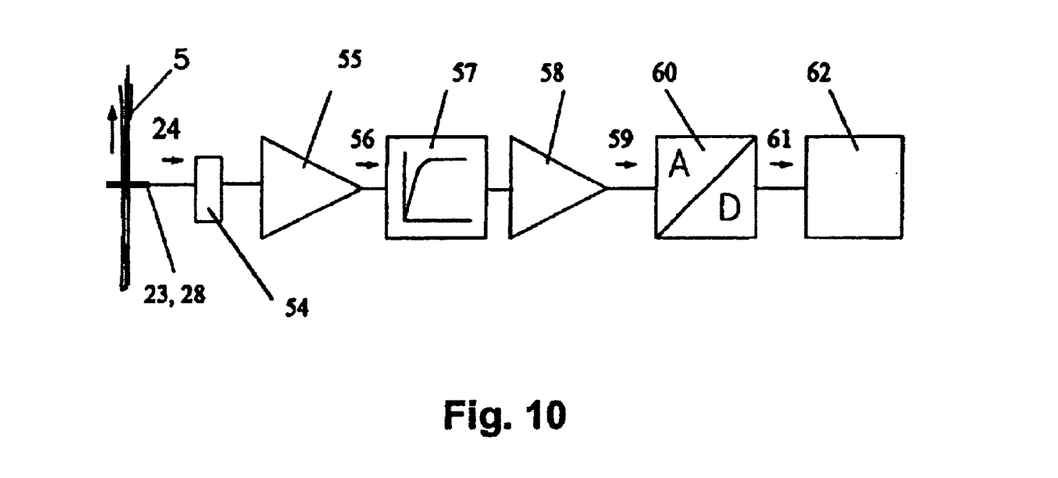
FIG. 10 is a simplified schematic circuit diagram of a detection circuit in accordance with the present invention.

A variety of front-end measurement circuits between the output electrode 23, 28 and the measurement circuit proper have been tested with the various electrode arrangements mentioned above. A schematic representation of a measuring circuit in accordance with the present invention is shown in FIG. 10. The signals 24 from the relevant output electrode 23, 28 is amplified by an amplifier 55. Before amplification it may pass through front end measurement circuit 54 which will be described below.

The variations in the amplified signal 56 are amplified, via a filter 57, in an AC voltage amplifier 58. The filter 57 may be a high pass filter but may also be a band-pass filter. The output signal 59 from the AC voltage amplifier 58 is fed to an analog-to-digital converter 60. The data 61 from the analog-to-digital converter 60 are processed further by a programmable digital computer 62. The decision circuit 47 may be implemented in digital computer 62.

A first type of front end circuit 54 includes a passive compensated resistor network. The relevant electrode 23, 28 is connected by a 10 MOhm resistor via a coaxial cable to the input of the amplifier 55 which had an input impedance of 1 MOhm.

A second type of front end circuit 54 includes a shunt resistor and a voltage follower buffer amplifier. The shunt resistor had a value of between 1 MOhm and 101 MOhm. The preferred shunt resistor value was 101 MOhm. Lower values of shunt resistor reduced the signal received drastically. The buffer amplifier was formed from an operational amplifier fed from a single +5 V source. To allow both positive and negative signals 24 in the amplifier output a 2.5 V voltage source was connected between the shunt resistor and earth. The parasitic capacitance across the shunt resistor limited the bandwidth to about 2 kHz.

A third type of front end circuit 54 includes a transimpedance amplifier. The transimpedance amplifier was constructed from an operational amplifier driven by a single +5 V source. To allow both positive and negative signals 24 to appear in the output of the amplifier, the amplifier was biased with 2.5 V on its non-inverting input. The transimpedance resistor had a value of 101 MOhm. A capacitance was placed across the resistor which limited the bandwidth to about 5 kHz.

In addition to the above, the present invention also includes the use of a high-pass circuit after the front end circuit. The high-pass circuit comprised had a cut-off frequency of either 25 Hz or 150 Hz. The high-pass circuit may be included as the filter 57.

In table 1 the bandwidths for the shunt resistor with the voltage follower buffer amplifier and the transimpedance amplifier are given in dependence on whether the output electrode 23, 28 was galvanically or capacitively or dielectrically coupled.

TABLE 1

| Type of coupling | High pass filter | Bandwidth transimpedance amplifier | Bandwidth shunt resistor with voltage follower |
|---|---|---|---|
| Dielectric/capacitive | None | 1 kHz–5 kHz | 1 kHz–2 kHz |
| Galvanic | None | DC–5 kHz | DC–2 kHz |
| Galvanic | 25 Hz | 25 Hz–5 kHz | 25 Hz–2 kHz |
| Galvanic | 150 Hz | 150 Hz–5 kHz | 150 Hz–2 kHz |

Figure 11A:
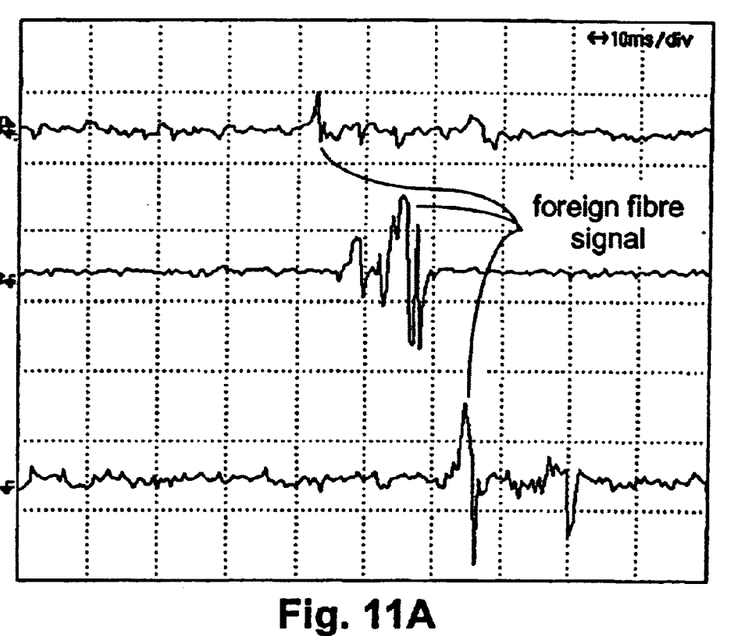
FIGS. 11A and 11B show traces of triboelectric signals from cotton including polyproplene foreign matter.
Figure 11B:
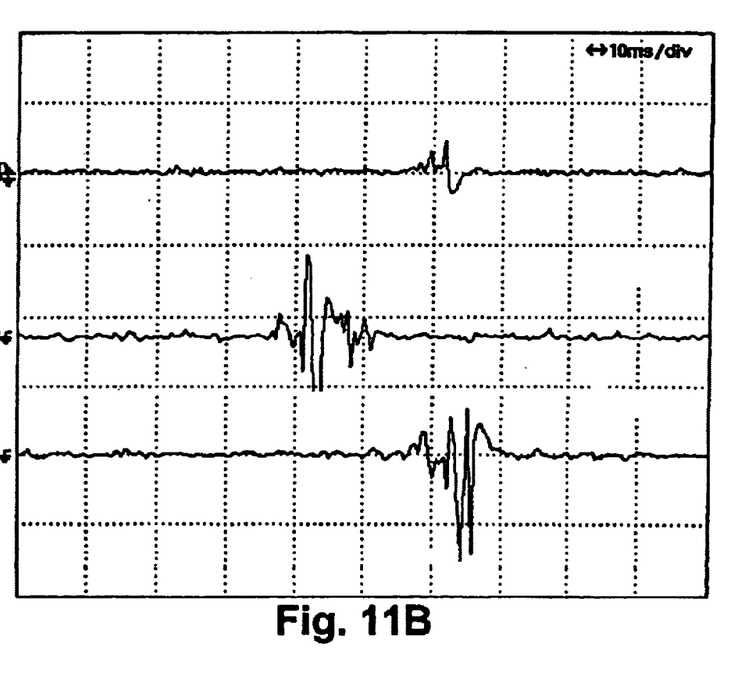

The discrimination criterion for foreign material was based on the ratio of the instantaneous signal 24 to the yarn noise. Typically received signals for a galvanically and a dielectrically coupled electrodes are shown in FIGS. 11A and B. To calculate the foreign fibre signal/yarn noise ratio the peak-to-peak value of the signal from the foreign fibre was measured at least three times. The selection criterion for deciding if foreign material is present may a sensitivity which is defined as the ratio between the peak-to-peak value of the signal picked-up from a foreign material, e.g. a PP fibre, and the standard deviation of the yarn noise signal. This sensitivity is related to the signal-to-noise ratio for the detection system. A higher sensitivity value represents a higher signal-to-noise ratio and therefore a better chance of discrimination.

For distinguishing polypropylene foreign matter in cotton yarn the galvanically coupled electrodes performed somewhat better than the dielectrically or capacitively coupled electrodes. This may be due to the less favourable high pass cut-off frequency of the dielectric coupling and the greater triboelectric charge when cotton comes in contact with a dielectric material such as glass. This increases the yarn base signal thus worsening the foreign fibre signal/yarn noise signal ratio. In accordance with any of the embodiments of the present invention it is preferred if the pick-up electrode material is selected so that the foreign fibre signal/yarn noise signal is maximised. This may include selecting a material for the pick-up electrode which minimises the yarn base signal amplitude, e.g. the use of a conductive pick-up electrode directly in contact with the yarn 5.

Figure 12:
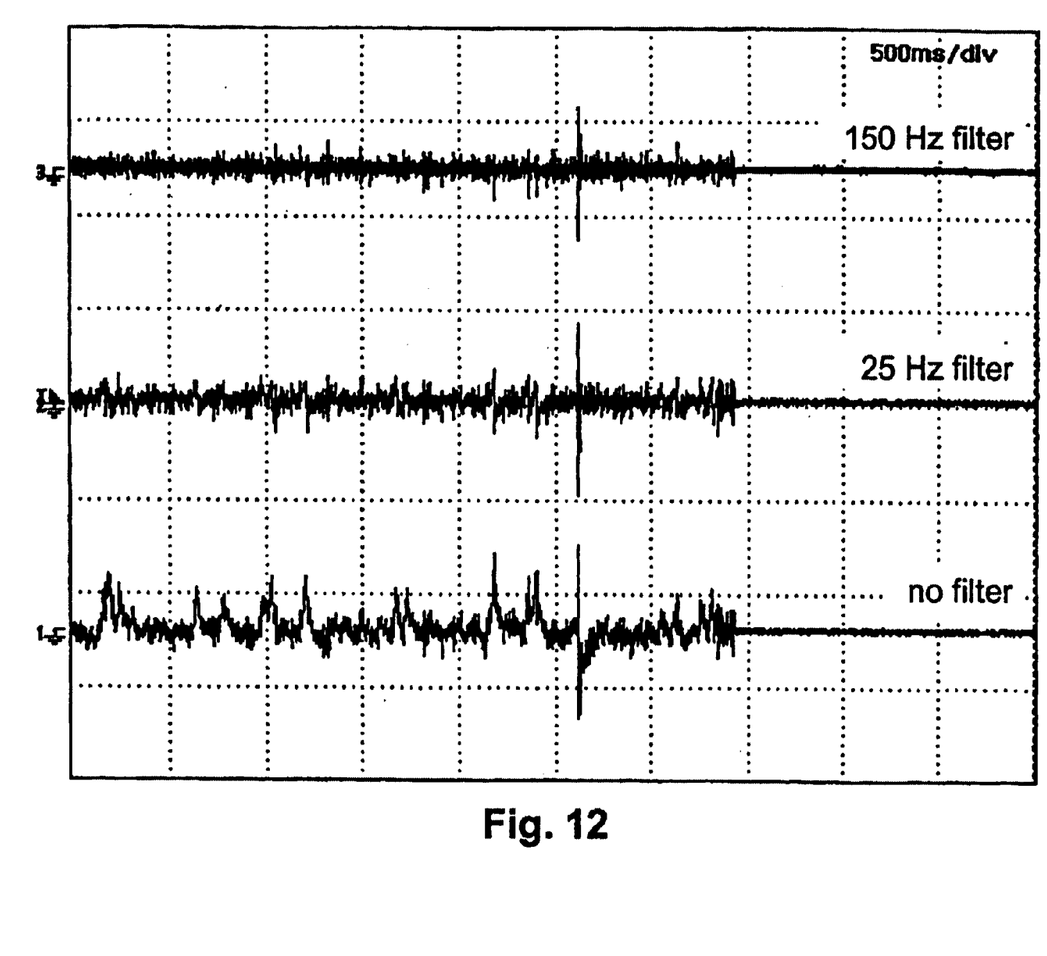
FIG. 12 shows three traces of triboelectric signals, the top trace being with a high pass filter of 150 Hz, the middle trace being with a high pass filter of 25 Hz, and the bottom trace being without filter.

The bandwidth of frequencies detected by the front end and amplification circuitry influenced the results of detecting polypropylene foreign material in cotton. The transimpedance amplifier with a high cut-off frequency of about 5 kHz gave better results than the shunt resistor/voltage follower with an upper cut-off frequency of 2 kHz. Also the elimination of low frequency and DC components improved discrimination of the signal. The 25 Hz high pass filter had a positive influence on the results and a 150 Hz high pass filter gave the best results as can be seen from FIG. 12. In FIG. 12 the top trace 3 is measured using a 150 Hz high pass filter, the middles trace 2 with a 25 Hz high pass filter and the bottom trace 1 with no filter, i.e. the available bandwidth. The top trace has the smallest yarn noise signal, thus providing the best foreign fibre signal/yarn noise ratio. This is because the DC and low-frequency components in the signal increase the base yarn noise signal without adding further power into the foreign fibre signal. It is assumed that the most important energy spectrum for the polypropylene foreign fibres lies between 25 Hz and 5 kHz. In accordance with all the embodiments of the present invention it is preferred if the operation or the design of detector 40, e.g. electrode arrangement and measurement circuit, is selected so that those frequencies are detected which contain the most information about the presence of foreign materials and/or contain the least amount of energy from the yarn noise signal. In particular, it is preferred if the bandwidth of the signals which pass through the measuring circuit 43 of FIG. 1 is selected to optimise the foreign fibre signal to yarn noise signal.

Figure 13:
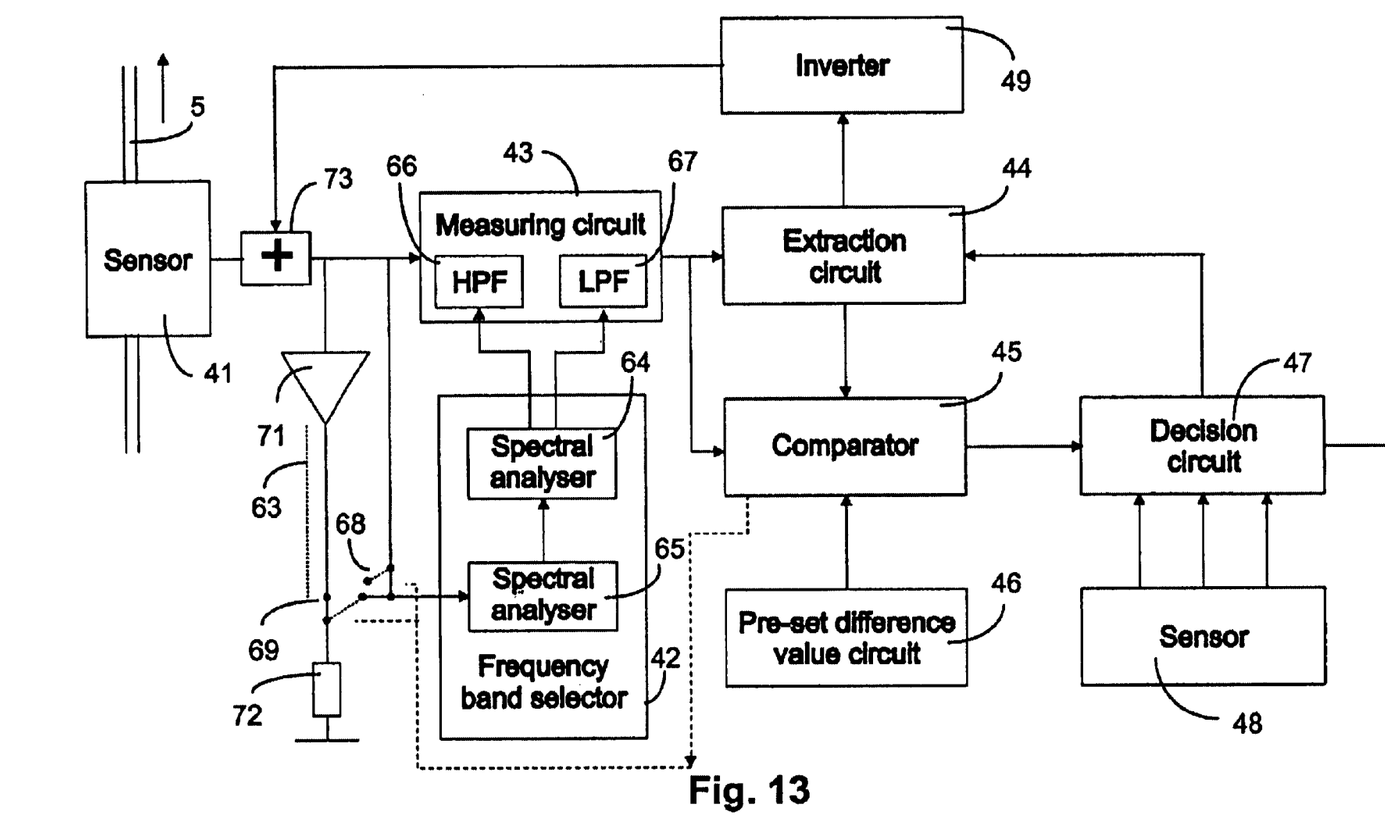
FIG. 13 is a schematic circuit diagram of a detector circuit in accordance with the present invention which includes automatic, dynamic control of the high and low pass filters of the measuring circuit as well as cancellation of periodic disturbances from the triboelectric signal.

An embodiment of the frequency bandwidth selector 42 (see FIG. 1) is shown schematically in FIG. 13. The measuring circuit 43 includes a tunable high pass filter 66 and a tunable low pass filter 67. Any amplifier used in the measuring circuit 43 preferably has a large bandwidth. The filters 66 and 67 define a bandwidth of signals transmitted through the measuring circuit 43. Frequency band selector 42 may be permanently attached to the measuring circuit 43 and may continuously and dynamically change the frequency bandwidth of the measuring circuit 43. Alternatively, the frequency band selector 42 may be a portable device which is plugged into the measuring circuit 43 and connected to the triboelectric sensor output only on set up or during routine quality control tests.

The signal from the triboelectric sensor 41 after cancelling of periodic disturbances in the adder 73 (see above description relating to FIG. 1) is fed in parallel to the measuring circuit 43 and a spectral analyser 64 of the frequency selector 42 via a normally closed switch 68. The spectral analyser 64 generates a first frequency/signal power spectrum for the yarn noise signal from the signal received directly from the adder 73 and this first spectrum is supplied to processor 64. A part of the signal from the adder 73 is fed via a low gain, high input impedance amplifier 71 and a normally closed switch 69 to a delay line 63 which is terminated by a non-reflecting, matched impedance 72. The delay line 63 should be long enough to effectively store the periodic signal cancelled output signal from the adder 73 for a sufficient time to capture a foreign material signal within the response time of the foreign material detecting system. For example, the delay line 63 should be long enough to store the signal from 500 mm of yarn or more. When a foreign material signal is output by comparator 45, a signal from the comparator causes switches 68 and 69 to be thrown so that the output of the delay line 63 is disconnected from the impedance 72 and fed to the spectral analyser 65 and the direct connection of the analyser 64 to the adder 73 is broken. The spectral analyser 64 then generates a second frequency/energy spectrum of the signal on the delay line 63 which includes the spectra of the yarn signal cancelled of periodic signals and the foreign material signal. This second spectrum is supplied to the processor 64 which subtracts the first spectrum from the second spectrum to obtain a third spectrum which is representative of the foreign matter signal cleaned of the spectra of any periodic signals and of the yarn noise.

Figure 14A:
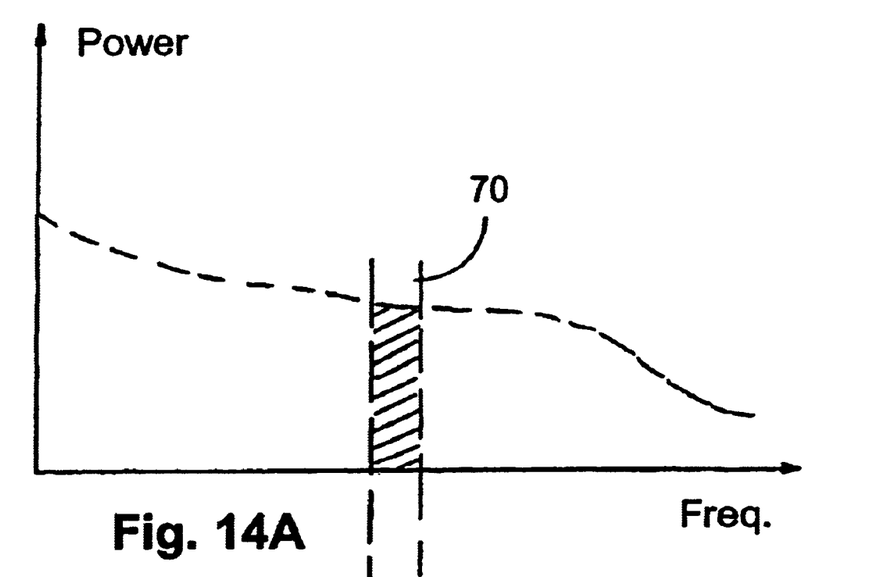
FIGS. 14A and 14B are arbitrary spectra for understanding the selection of upper and lower filter cut-off frequencies for the filters in the measuring circuit from the spectra of yarn noise and foreign material signals, respectively, in accordance with an embodiment of the present invention.
Figure 14B:
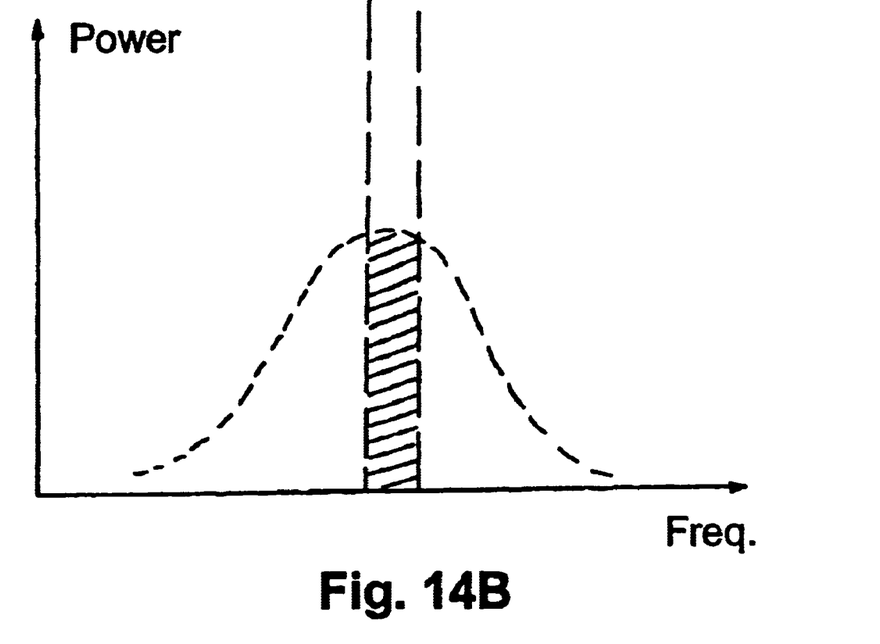

Two arbitrary first and third frequency/power spectra are shown in FIGS. 14A and B for the yarn noise and the foreign material signal respectively. Processor 64 determines from the spectra which bandwidth provides an optimal signal-to-noise ratio. For instance, the spectra may be divided into a plurality of contiguous narrow frequency bands 70. For each band 70, processor 64 calculates the energy in the foreign material signal and in the yarn noise signal (are under the respective curve) and calculates the ratio of these two energies for each band 70. This ratio provides an estimate of the signal-to-noise ratio within that frequency band. Once all the energy ratios have been calculated for all the frequency bands 70, processor 64 can determine an optimised bandwidth and then set the tunable low and high pass filters 67, 66 to the upper and lower frequency cut-offs accordingly. For instance, processor 64 may optimise the bandwidth based on one or more of the following criteria:

maximising the energy of the foreign material signal transmitted through the measuring circuit 43, minimising the energy of the yarn noise signal transmitted through circuit 43, maximising the ratio of the energies of the foreign material signal to the yarn noise signal transmitted through circuit 43, maximising the ratio of the energies of the foreign material signal to the yarn noise signal while maintaining at least a minimum energy in the foreign material signal transmitted through circuit 43.

Figure 15A:
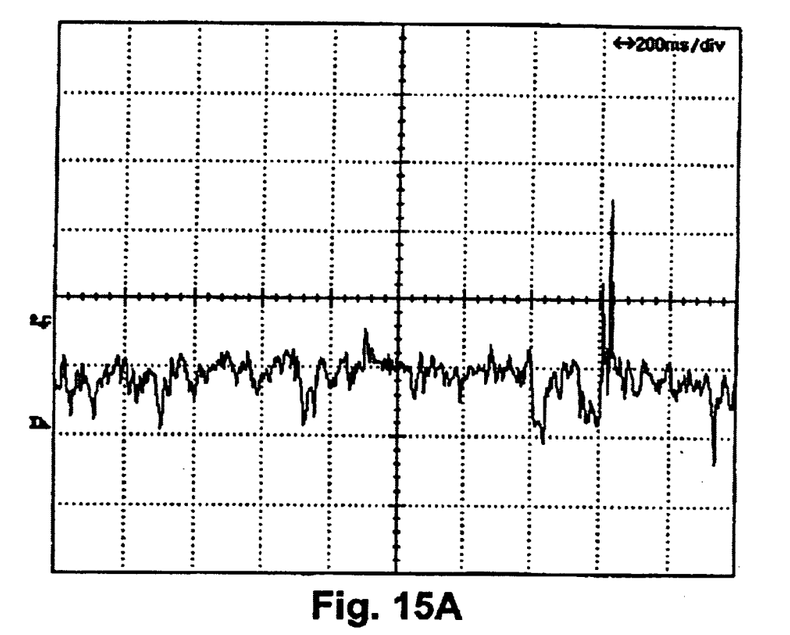
FIG. 15A is a trace of a triboelectric signal from cotton yarn including a polypropylene foreign fibre.
Figure 15B:
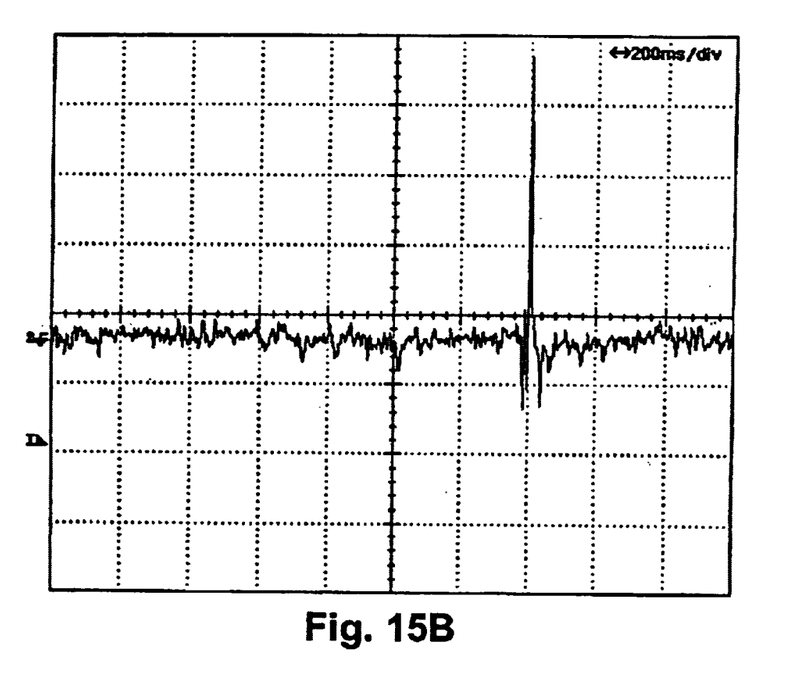
FIG. 15B shows the trace of the same polypropylene foreign fibre in cotton yarn when an external remote charge stripper is used to remove charge from the cotton yarn. The signal-to-noise ratio is improved compared to the trace of FIG. 13A.

The use of charge stripper electrodes adjacent to the pick-up electrode and/or remote therefrom is preferred in accordance with the present invention. Remote charge stripper electrodes are most preferred. This is seen in a comparison of FIGS. 15A and B, in which FIG. 15B shows the result of FIG. 15A with an additional remote stripper electrode. The signal/nose ratio of FIG. 15B is considerable higher. For instance, it is preferred if the torque stop 2 is made from a conductive material which is earthed and is used as a charge stripper. Further, biasing a stripper electrode may provide advantageous results.

It is preferred if temperature and humidity are kept as constant as possible. Therefore, it is preferred if all materials are equilibrated at shop temperature and humidity levels before being used on the spinning machine. In addition it is preferred if dust is kept to a minimum along the yarn path.

Foreign material as used above refers to material which is not intended to be in the textile material, e.g. comes from another source. It is usually differs from the textile material. The foreign material may itself be a textile material.

While the invention has been shown and described with reference to preferred embodiments, it will be understood by those skilled in the art that various changes or modifications in form and detail may be made without departing from the scope and spirit of this invention as defined in the attached claims. For example the foreign material detector in accordance with the present invention may be included in a card, a drawing bench, a ring spinning machine, an air-jet spinning machine, an open-end spinning machine, a chemical spinning machine, a bobbin winding machine a doubling machine, a combing machine, a bobbin frame, a texturing machine and a loom.

Further, the detector circuits described above mainly include analog circuit elements but the present invention is not limited thereto. For instance the triboelectric signals picked up from the moving textile material may be converted to digital signals preferably at a high sampling frequency and all signal processing then performed in the digital domain.

I claim:

1. A method for detecting discrete foreign fibers in a moving textile material, in particular in moving threads, yarns or slivers, comprising the steps of:

generating relative motion between the textile material and a probe;

measuring triboelectric signals picked up by the probe from the textile material;

comparing the measured triboelectrical signals with a value representative of the textile material without foreign fibers; and determining from the result of the comparison whether a discrete foreign fiber is present in the textile material.

2. The method according to claim 1, wherein the comparing step includes extracting a signal level from the measured triboelectric signals to provide the value representative of the textile material without foreign fibers.

3. The method according to claim 2, wherein the extracting step includes cancelling periodic variations of the measured triboelectric signals.

4. The method according to claim 2, wherein the value representative of the textile material without discrete foreign fibers is continuously monitored by a running standard deviation over a suitable length of the textile material.

5. The method according to claim 4, wherein the comparing step includes feeding the measured triboelectric signals to a comparator, said comparator comparing the value representative of the textile material without discrete foreign fibers to the measured triboelectric signals and determining the difference therebetween, at least one pre-set value being used to determine whether the difference between the value representative of the textile material without discrete foreign fibers and the measured triboelectric signals exceeds the at least one pre-set difference value.

6. The method according to claim 5, further comprising the step of normalizing a peak-to-peak value of the measured triboelectric signals with respect to the value representative of the textile material without discrete foreign fibers prior to being compared therewith.

7. The method according to claim 1, wherein the measuring step includes selecting a frequency range of the measured triboelectric signals in accordance with one of the following: the energy of the triboelectric signals generated by the moving textile material without a discrete foreign fiber is a minimum in the frequency range, the energy of the triboelectric signals generated by a discrete foreign fiber is a maximum in the frequency range, the ratio of the energies of the triboelectric signals generated by the moving textile material and a discrete foreign fiber is a maximum in the frequency range, the ratio of the energies of the triboelectric signals generated by the moving textile material and a discrete foreign fiber is a maximum in the frequency range and the energy of the triboelectric signals generated by a discrete foreign fiber in the frequency range is greater than a minimum value.

8. The method according to claim 1, further comprising the step of stripping charge from the moving textile material before the measuring step.

9. An apparatus for detecting discrete foreign fibers in a moving textile material, in particular in moving threads, yarns or slivers, comprising:

a probe for picking up triboelectric signals from the textile material;

a comparator for comparing an output of the probe with a reference value and being adapted to provide a signal representative of detection of a discrete foreign fiber in the textile material and means responsive to the detection signal for determining whether a discrete foreign fiber is present in the textile material.

10. The apparatus according to claim 9, wherein the probe includes a conductive electrode in galvanic contact with the textile material.

11. The apparatus according to claim 9, wherein the probe includes a conductive electrode capacitively or dielectrically coupled to the textile material.

12. The apparatus according to claim 11, wherein the probe includes an insulating material in contact with the textile material and the conducting electrode is insulated by the insulating material from the textile material.

13. The apparatus according to claim 12, further comprising a measuring circuit connected between the probe and the comparator for filtering the output of the probe.

14. The apparatus according to claim 9, further comprising an extraction circuit for extracting a signal level from measured triboelectric signals to provide a value representative of the textile material without a discrete foreign fiber.

15. The apparatus according to claim 14, wherein the comparator is arranged to continuously monitor the triboelectric signals by a running standard deviation over a suitable length of the textile.

16. The apparatus according to claim 15, wherein the comparator is arranged to normalize a peak-to-peak value of measured triboelectric signals with respect to a value representative of the textile material without discrete foreign fibers.

17. The apparatus according to claim 9, further comprising a charge stripper electrode in contact with the textile material located before the probe with reference to the movement of the textile material.

18. The apparatus according to claim 9, further comprising a cancellation circuit for cancelling out periodic signal variations from the output of the probe.

19. The apparatus according to claim 9, further comprising a device for selecting a frequency range for the signals sent from the probe to the comparator based on one of the following: the energy of the triboelectric signals generated by the moving textile material without discrete foreign fibers is a minimum in the frequency range, the energy of the triboelectric signals generated by a discrete foreign fiber is a maximum in the frequency range, the ratio of the energies of the triboelectric signals generated by the moving textile material and discrete foreign fibers is a maximum in the frequency range, and the ratio of the energies of the triboelectric signals generated by the moving textile material and discrete foreign fibers is a maximum in the frequency range and the energy of the triboelectric signals generated by discrete foreign fibers in the frequency range is greater than a minimum value.

20. The apparatus according to claim 9, mounted in a card, a drawing bench, a ring spinning machine, a air-jet spinning machine, an open-end spinning machine, a chemical spinning machine, a bobbin winding machine, a doubling machine, a combing machine, a bobbin frame, a texturing machine or a loom.

21. The apparatus according to claim 9, further comprising:

a measuring circuit connected between the probe and the comparator for filtering the output of the probe;

an extraction circuit for extracting a signal level from the measured triboelectric signals to provide a value representative of the textile material without discrete foreign fibers;

a charge stripper electrode in contact with the textile material located before the probe with reference to the movement of the textile material;

a cancellation circuit for cancelling out periodic signal variations from the output of the probe;

a device for selecting a frequency range for the signals sent from the probe to the comparator based on one of the following: the energy of the triboelectric signals generated by the moving textile material without discrete foreign fibers is a minimum in the frequency range, the energy of the triboelectric signals generated by discrete foreign fibers is a maximum in the frequency range, the ratio of the energies of the triboelectric signals generated by the moving textile material and discrete foreign fibers is a maximum in the frequency range, and the ratio of the energies of the triboelectric signals generated by the moving textile material and discrete foreign fibers is a maximum in the frequency range and the energy of the triboelectric signals generated by discrete foreign fibers in the frequency range is greater than a minimum value.

22. The apparatus according to claim 21, wherein the probe includes a conductive electrode in galvanic contact with the textile material.

23. The apparatus according to claim 21, wherein the probe includes a conductive electrode capacitively or dielectrically coupled to the textile material.

24. The apparatus according to claim 23, wherein the probe includes an insulating material in contact with the textile material and the conducting electrode is insulated by the insulating material from the textile material.

* * * * *